United States Patent
Fujinuma

(10) Patent No.: US 11,759,099 B2
(45) Date of Patent: Sep. 19, 2023

(54) OPTICAL SCANNING IMAGING/PROJECTION APPARATUS AND ENDOSCOPE SYSTEM

(71) Applicant: OLYMPUS CORPORATION, Tokyo (JP)

(72) Inventor: Ken Fujinuma, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 1030 days.

(21) Appl. No.: 16/042,185

(22) Filed: Jul. 23, 2018

(65) Prior Publication Data

US 2018/0325365 A1    Nov. 15, 2018

Related U.S. Application Data

(63) Continuation of application No. PCT/JP2016/055994, filed on Feb. 29, 2016.

(51) Int. Cl.
*A61B 1/00* (2006.01)
*H05B 47/155* (2020.01)
(Continued)

(52) U.S. Cl.
CPC ........ *A61B 1/0655* (2022.02); *A61B 1/00006* (2013.01); *A61B 1/00009* (2013.01);
(Continued)

(58) Field of Classification Search
CPC ............ A61B 2090/366; A61B 5/0071; A61B 5/0084; A61B 5/0062; A61B 1/00006; H05B 47/105
See application file for complete search history.

(56) References Cited

U.S. PATENT DOCUMENTS

| 5,772,593 A * | 6/1998 | Hakamata ............... A61B 90/36 348/77 |
| 10,080,623 B2 * | 9/2018 | Saito ...................... A61B 34/20 |

(Continued)

FOREIGN PATENT DOCUMENTS

| JP | 2009516568 A | 4/2009 |
| JP | 2010115391 A | 5/2010 |

(Continued)

OTHER PUBLICATIONS

Lee et al. "Scanning fiber endoscopy with highly flexible, 1 mm catheterscopes for wide-field, full-color imaging." J Biophoton, vol. 3, No. 5-6, Mar. 25, 2010, pp. 385-407. (Year: 2010).*

(Continued)

*Primary Examiner* — Angela M Hoffa
(74) *Attorney, Agent, or Firm* — Scully, Scott, Murphy & Presser, P.C.

(57) ABSTRACT

An optical scanning imaging/projection apparatus includes a light source that outputs illumination light and projection light in the visible range, an optical scanner that scans the illumination light and the projection light, which are output from the light source, along a predetermined scanning trajectory, a switch that switches the output from the light source so that the illumination light and the projection light are alternately output, an optical detector that detects observation light generated by a subject irradiated with the illumination light, a storage that stores data in which an intensity of the detected observation light detected is associated with information indicating a detection position on the scanning trajectory, and a projection light controller that controls, on the basis of the data stored in the storage unit, an intensity of the projection light to be applied to each position on the scanning trajectory.

15 Claims, 16 Drawing Sheets

(51) Int. Cl.
  *H05B 47/105*  (2020.01)
  *A61B 1/06*   (2006.01)
  *A61B 1/04*   (2006.01)
  *G02B 26/10*  (2006.01)
  *G01N 21/64*  (2006.01)
  *A61B 5/00*   (2006.01)
  *G03B 21/20*  (2006.01)
  *H04N 23/56*  (2023.01)
  *A61B 1/07*   (2006.01)
  *A61N 5/06*   (2006.01)
  *A61B 90/00*  (2016.01)
  *A61B 90/30*  (2016.01)

(52) U.S. Cl.
  CPC .......... *A61B 1/00172* (2013.01); *A61B 1/043* (2013.01); *A61B 1/0638* (2013.01); *A61B 1/0646* (2013.01); *A61B 1/0669* (2013.01); *A61B 1/07* (2013.01); *A61B 5/0062* (2013.01); *A61B 5/0071* (2013.01); *A61B 5/0084* (2013.01); *G01N 21/6456* (2013.01); *G02B 26/103* (2013.01); *G03B 21/204* (2013.01); *H04N 23/56* (2023.01); *H05B 47/105* (2020.01); *H05B 47/155* (2020.01); *A61B 1/00186* (2013.01); *A61B 90/30* (2016.02); *A61B 2090/366* (2016.02); *A61B 2090/373* (2016.02); *A61N 5/0601* (2013.01)

(56) References Cited

U.S. PATENT DOCUMENTS

| | | | | |
|---|---|---|---|---|
| 10,151,914 B2* | 12/2018 | Mori | ................. | G02B 23/2484 |
| 10,151,916 B2* | 12/2018 | Mori | ................. | A61B 1/00057 |
| 10,579,891 B2* | 3/2020 | Abbas | ................. | A61B 5/7445 |
| 10,754,143 B2* | 8/2020 | Fujinuma | ............. | G02B 26/103 |
| 10,758,112 B2* | 9/2020 | Fujinuma | ............... | G02B 23/26 |
| 10,859,816 B2* | 12/2020 | Fujinuma | ................. | A61B 1/00 |
| 11,054,565 B2* | 7/2021 | Shimamoto | ........ | G02B 23/2423 |
| 11,375,883 B2* | 7/2022 | Takata | ..................... | A61B 1/07 |
| 2008/0004533 A1* | 1/2008 | Jansen | .................. | A61B 5/415 |
| | | | | 600/476 |
| 2009/0028407 A1 | 1/2009 | Seibel et al. | | |
| 2010/0123775 A1 | 5/2010 | Shibasaki | | |
| 2012/0241620 A1 | 9/2012 | On | | |
| 2015/0374452 A1* | 12/2015 | Saito | ................... | A61B 5/0071 |
| | | | | 600/424 |
| 2016/0252716 A1* | 9/2016 | Nakamura | ............. | A61B 90/00 |
| | | | | 348/79 |
| 2017/0046586 A1* | 2/2017 | Abbas | .................. | G06K 9/3233 |
| 2017/0079741 A1* | 3/2017 | Makinouchi | .......... | A61B 90/00 |
| 2017/0099421 A1 | 4/2017 | Nakajima | | |
| 2017/0236022 A1* | 8/2017 | Abbas | .................. | G06K 9/3233 |
| | | | | 348/77 |
| 2018/0014901 A1* | 1/2018 | Saito | ...................... | A61B 90/00 |
| 2020/0319431 A1* | 10/2020 | Nam | ..................... | G02B 13/16 |
| 2021/0021793 A1* | 1/2021 | Takada | ..................... | G09G 5/00 |

FOREIGN PATENT DOCUMENTS

| | | |
|---|---|---|
| JP | 2010284189 A | 12/2010 |
| JP | 2011005002 A | 1/2011 |
| JP | 2011125404 A | 6/2011 |
| JP | 2015136580 A | 6/2015 |
| JP | 2015136580 A | 7/2015 |
| JP | 2016002406 A | 1/2016 |

OTHER PUBLICATIONS

International Search Report dated May 24, 2016 issued in PCT/JP2016/055994.

* cited by examiner

| ADDRESS | INTENSITY VALUE |
|---------|-----------------|
| 0 | $D_0$ |
| 1 | $D_1$ |
| 2 | $D_2$ |
| ⋮ | ⋮ |
| $N_{end}$ | $D_{N_{end}}$ |

FIG. 15

| ADDRESS | | DATA D |
|---|---|---|
| Y | X | |
| 0 | 0 | D(0, 0) |
| 0 | 1 | D(1, 0) |
| 0 | 2 | D(2, 0) |
| ... | ... | ... |
| 0 | $X_{max}$ | D($X_{max}$, 0) |
| 1 | 0 | D(0, 1) |
| 1 | 1 | D(1, 1) |
| 1 | 2 | D(2, 1) |
| ... | ... | ... |
| y | x | D(x, y) |
| ... | ... | ... |
| ... | ... | ... |
| $Y_{max}$ | $X_{max}$ | D($X_{max}$, $Y_{max}$) |

OPTICAL SCANNING IMAGING/PROJECTION APPARATUS AND ENDOSCOPE SYSTEM

CROSS-REFERENCE TO RELATED APPLICATIONS

This is a continuation of International Application PCT/JP2016/055994, with an international filing date of Feb. 29, 2016, which is hereby incorporated by reference herein in its entirety.

TECHNICAL FIELD

The present invention relates to an optical scanning imaging/projection apparatus and an endoscope system.

BACKGROUND ART

There is known an endoscope apparatus equipped with a videoscope and a scanning endoscope insertable into a forceps channel of the videoscope, with which white-light observation with the videoscope and fluorescence observation with the scanning endoscope are performed simultaneously so as to display a composite image constituted by a white-light image and a fluorescence image superimposed on each other (for example, refer to Japanese Unexamined Patent Application, Publication No. 2011-5002).

SUMMARY OF INVENTION

An object of the present invention is to provide an optical scanning imaging/projection apparatus and an endoscope system, with which two types of subject images superimposed on each other without displacement can be observed without requiring a special sophisticated processor.

A first aspect of the present invention provides an optical scanning imaging/projection apparatus that includes a light source that is configured to output illumination light and projection light, the projection light being in the visible range; an optical scanner that is configured to scan the illumination light and the projection light, which are output from the light source, along a predetermined scanning trajectory; a switch that is configured to switch the output from the light source so that the illumination light and the projection light are alternately output; an optical detector that is configured to detect observation light generated by a subject irradiated with the illumination light; a storage that is configured to store data in which an intensity of the observation light detected with the optical detector is associated with information indicating a detection position on the scanning trajectory; and a projection light controller that is configured to control an intensity of the projection light to be applied to each position on the scanning trajectory, wherein the projection light controller comprises one or more processors, the one or more processors are configured to control the intensity of the projection light on the basis of the data stored in the storage.

In the first aspect described above, the switch may switch between the illumination light and the projection light every frame cycle unit.

In the first aspect described above, the switch may switch between the illumination light and the projection light either every detection cycle unit of the observation light by the optical detector or every scan cycle unit of the illumination light and the projection light by the optical scanner.

In the first aspect described above, the light source may output, as the illumination light, excitation light that excites fluorescence contained in the subject, and the optical detector may be equipped with an excitation light cut filter that is configured to block the excitation light and transmit the fluorescence, and may detect the fluorescence that has passed through the excitation light cut filter.

In the first aspect described above, the light source may output, as the illumination light, infrared light.

In the first aspect described above, the light source may output therapeutic light for treating body tissue, and the switch may switch the output of the light source between the illumination light, the projection light, and the therapeutic light.

In the first aspect described above, the storage may store the order in which the observation light is detected with the optical detector as the information indicating the detection position, and may array the intensity of the observation light in accordance with the order within the data, and the one or more processors may control the intensity of the projection light according to the order of the intensity of the observation light within the data.

In the first aspect described above, the optical scanning imaging/projection apparatus may further include a coordinate calculator that is configured to calculate coordinates of the detection position of the observation light detected with the optical detector, and the storage may store the coordinates calculated by the coordinate calculator as the information indicating the detection position.

In the first aspect described above, the optical scanning imaging/projection apparatus may further include a data processor that is configured to process the data stored in the storage, and the one or more processors may control the intensity of the projection light on the basis of the data processed by the data processor.

A second aspect of the present invention provides an endoscope system that includes any of the optical scanning imaging projection apparatuses described above, and an endoscope apparatus that is configured to acquire an endoscopic image of the subject.

BRIEF DESCRIPTION OF DRAWINGS

FIG. 15 illustrates a modified example of a data table stored in the storage unit.

DESCRIPTION OF EMBODIMENTS

An optical scanning imaging/projection apparatus 1 and an endoscope system 100 according to one embodiment of the present invention will now be described with reference to the drawings.

Figure 1:
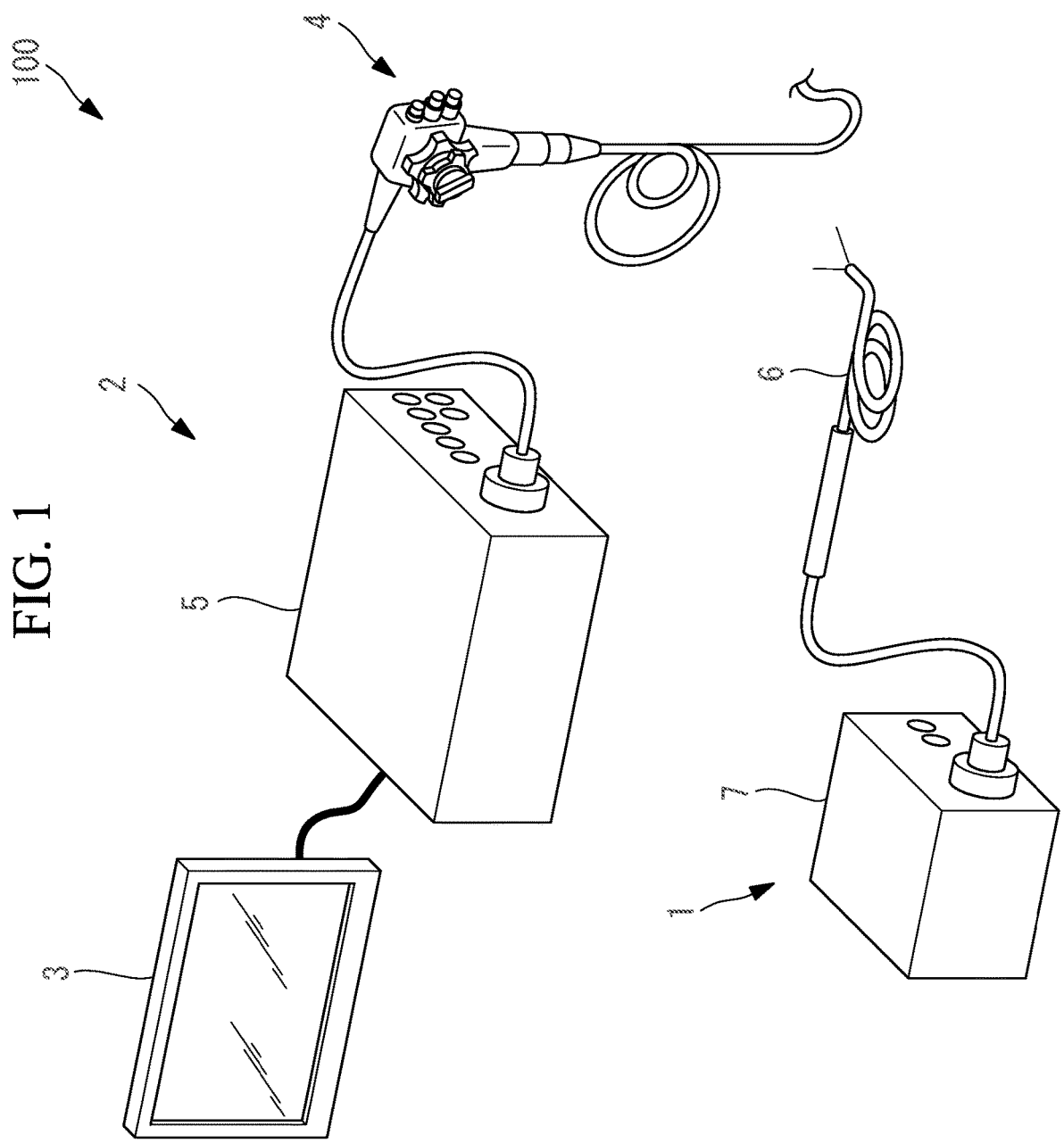
FIG. 1 is a diagram showing the overall configuration of an endoscope system according to one embodiment of the present invention.

As illustrated in FIG. 1, the endoscope system 100 according to this embodiment is equipped with the optical scanning imaging/projection apparatus 1, an endoscope apparatus 2, and a display apparatus 3 that displays an endoscopic image acquired through the endoscope apparatus 2.

The endoscope apparatus 2 is a typical endoscope apparatus and is equipped with an endoscope body 4 to be inserted into the body, and a processor 5 connected to a proximal end of the endoscope body 4. The endoscope body 4 includes an illuminating optical system (not illustrated) that emits white light from a distal end of the endoscope body 4, and an observation optical system (not illustrated) that receives light from body tissue, i.e., a subject A, and acquires the endoscopic image data. Inside the endoscope body 4, a treatment tool channel 4a that penetrates through the endoscope body 4 in the longitudinal direction is disposed.

Figure 2:
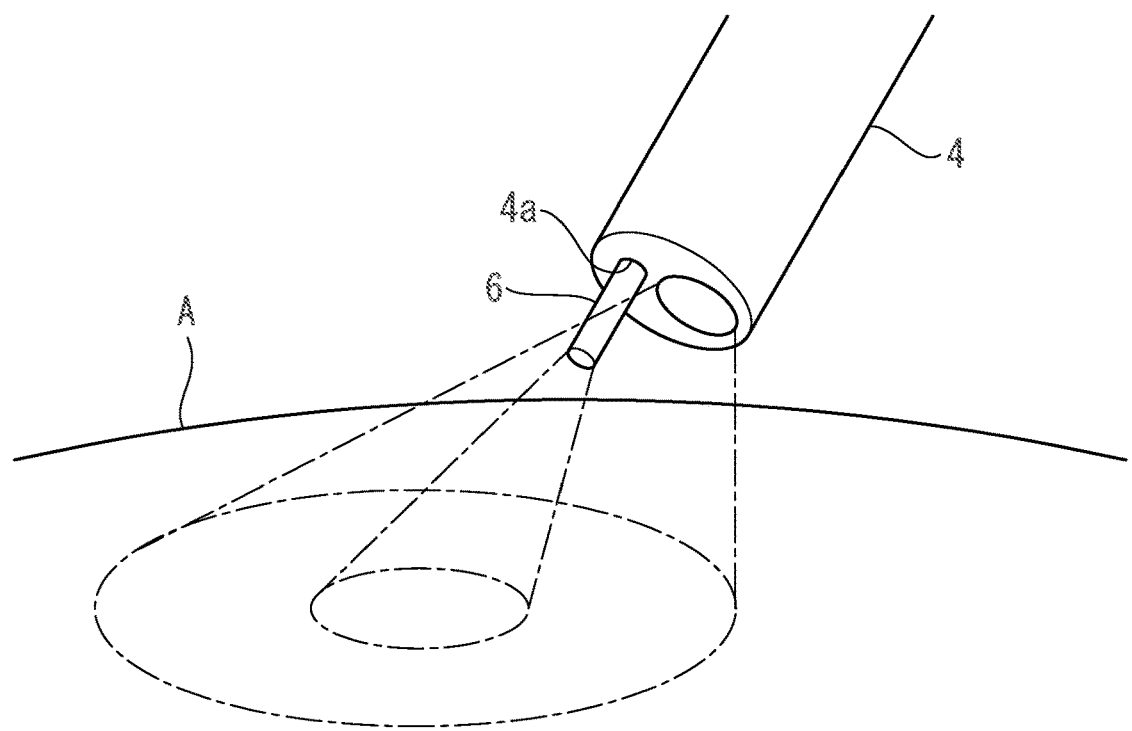
FIG. 2 is a diagram illustrating the operation state of the endoscope system illustrated in FIG. 1.
Figure 3:
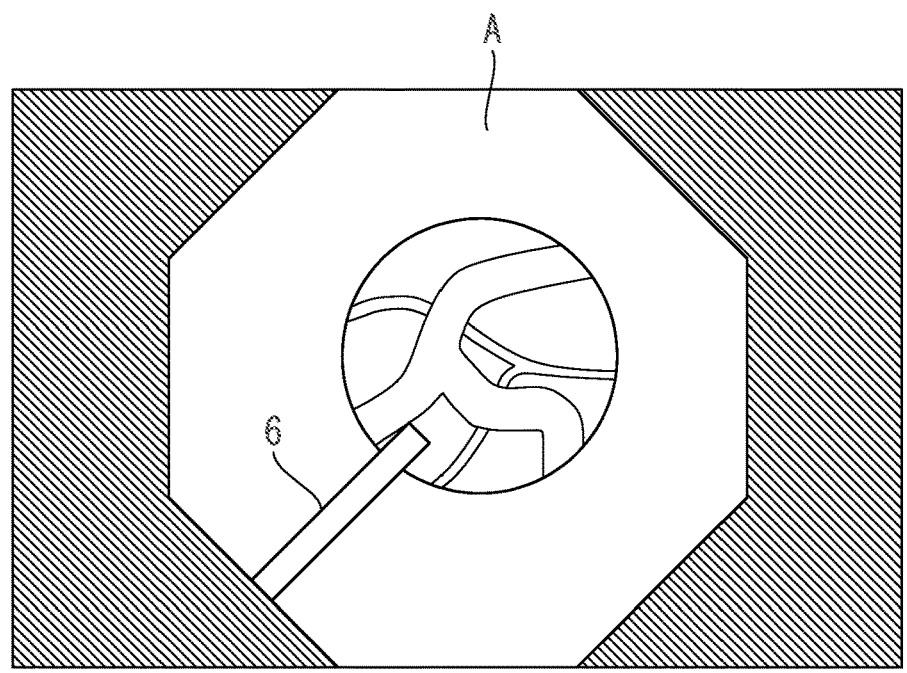
FIG. 3 is an example of an endoscopic image displayed on a display apparatus in the endoscope system illustrated in FIG. 1.

The optical scanning imaging/projection apparatus 1 is equipped with a long thin insertion portion 6, which can be inserted into the treatment tool channel 4a, and a controller device 7 connected to the proximal end of the insertion portion 6. During use, the insertion portion 6 is inserted into the treatment tool channel 4a so that the optical scanning imaging/projection apparatus 1 and the endoscope body 4 are integrated. As illustrated in FIGS. 2 and 3, the optical scanning imaging/projection apparatus 1 is designed so that, in this integrated state, the imaging range of the optical scanning imaging/projection apparatus 1 lies within the imaging range of the endoscope apparatus 2. FIG. 3 is an endoscopic image displayed on the display apparatus 3.

Figure 4:
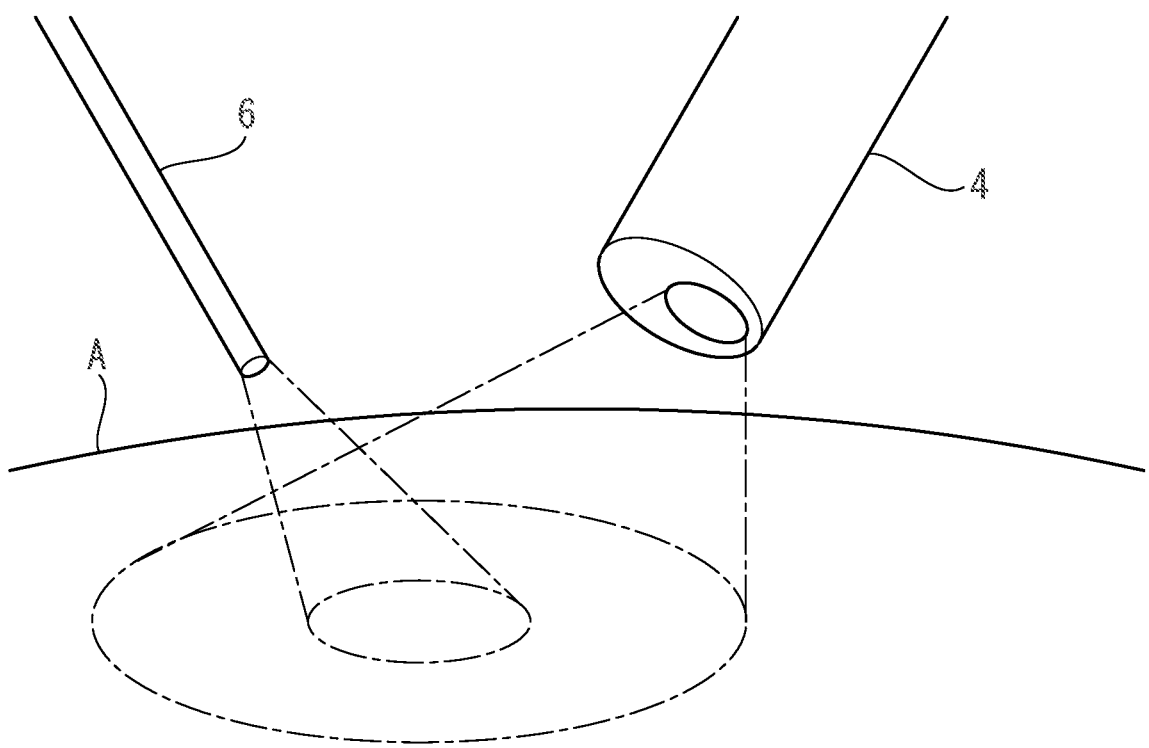
FIG. 4 is a diagram illustrating the operation state of a modified example of the endoscope system illustrated in FIG. 1.

Alternatively, as illustrated in FIG. 4, the optical scanning imaging/projection apparatus 1 and the endoscope apparatus 2 may be used separately. In this case, the relative position between the endoscope body 4 and the insertion portion 6 inside the body is adjusted so that the imaging range of the optical scanning imaging/projection apparatus 1 lies within the imaging range of the endoscope apparatus 2.

Next, detailed features of the optical scanning imaging/projection apparatus 1 are described.

Figure 5:
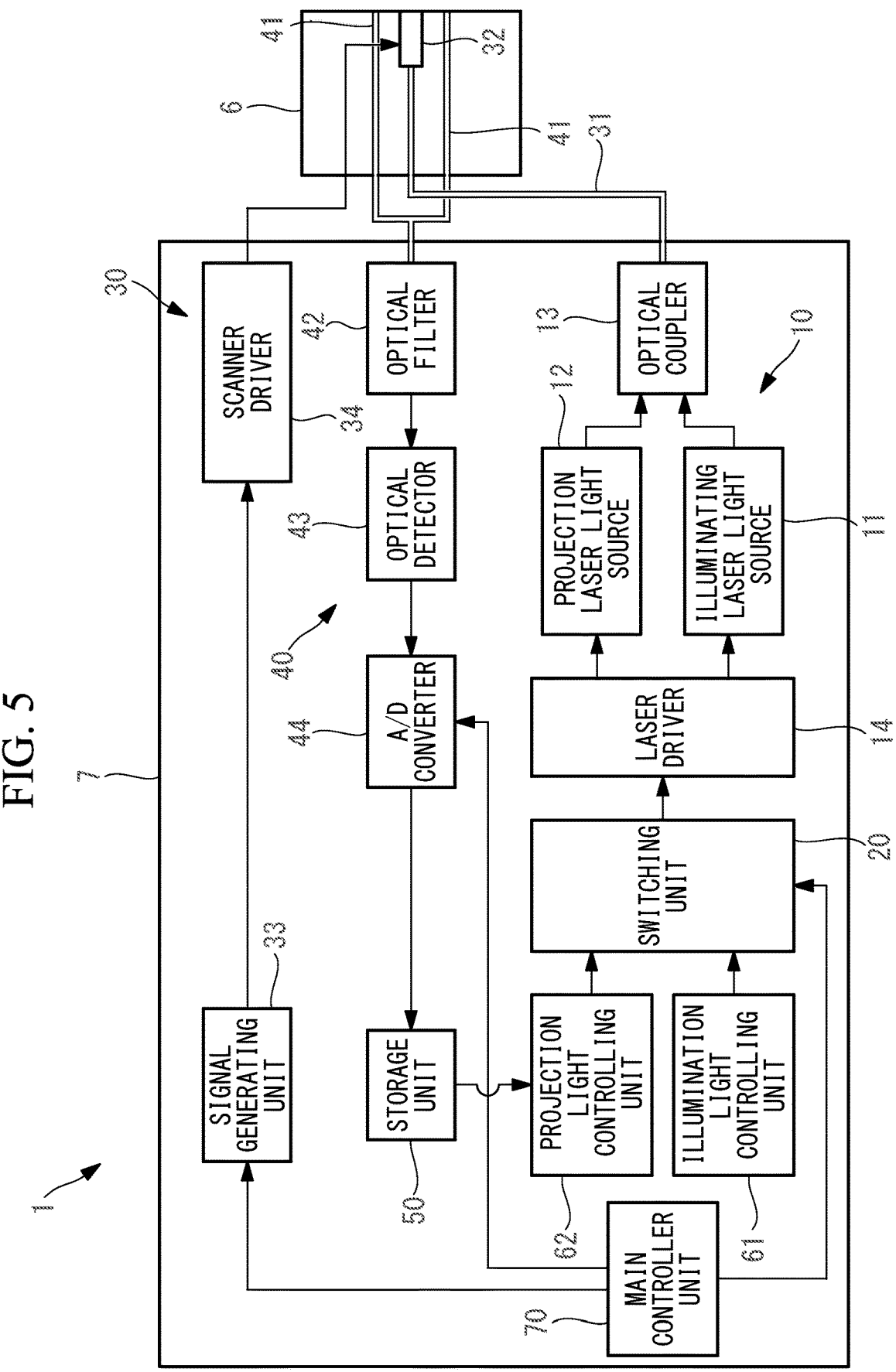
FIG. 5 is a functional block diagram of an optical scanning imaging/projection apparatus according to one embodiment of the present invention.

As illustrated in FIG. 5, the optical scanning imaging/projection apparatus 1 is equipped with a light source unit (light source) 10 that outputs illumination light and projection light; a switching unit (switch) 20 that switches the output of the light source unit 10 between illumination light and projection light; an optical scanning unit (optical scanner) 30 that scans the illumination light and the projection light, which are output from the light source unit 10, on the subject A; an optical detection unit (optical detector) 40 that detects observation light generated by the subject A irradiated with the illumination light; a storage unit (storage) 50 that stores the intensity of the observation light detected with the optical detection unit 40; an illumination light controlling unit (illumination light controller) 61 that controls the intensity of the illumination light; a projection light controlling unit (projection light controller) 62 that controls the intensity of the projection light; and a main controller unit (main controller) 70 that controls the switching unit 20, the optical scanning unit 30, and the optical detection unit 40.

The light source unit 10 is equipped with an illuminating laser light source 11 that outputs illumination light, a projection laser light source 12 that outputs projection light, an optical coupler 13, and a laser driver 14 that drives the laser light sources 11 and 12.

The illuminating laser light source 11 outputs, as the illumination light, a laser beam having an excitation wavelength of a fluorescent substance present within the subject A.

The projection laser light source 12 outputs, as the projection light, a laser beam in the visible range. The color of the projection light is preferably a color that has high visibility in the endoscopic image (for example, green).

The optical coupler 13 has two input terminals respectively coupled to the illuminating laser light source 11 and the projection laser light source 12, and one output terminal coupled to an optical fiber 31 for illumination. The optical coupler 13 outputs the illumination light and the projection light, which have been input from the illuminating laser light source 11 and the projection laser light source 12, to the optical fiber 31.

The laser driver 14 drives the illuminating laser light source 11 according to an illumination light control signal input from the illumination light controlling unit 61 through the switching unit 20, and drives the projection laser light source 12 according to a projection light control signal input from the projection light controlling unit 62 through the switching unit 20.

The switching unit 20 is controlled by the main controller unit 70 so that the switching unit 20 selects one of the illumination light control signal input from the illumination light controlling unit 61 and the projection light control signal input from the projection light controlling unit 62, and sends the selected signal to the laser driver 14. In this manner, the switching unit 20 drives the selected light source of the laser light sources 11 and 12 so that illumination light and projection light are alternately output from the light source unit 10.

The optical scanning unit 30 includes the optical fiber 31, a scanner 32 that is disposed at the distal end portion of the insertion portion 6 and scans the light emitted from the distal end of the optical fiber 31, a signal generating unit (signal generator) 33 that generates a scan drive signal on the basis of the scan control signal from the main controller unit 70, and a scanner driver 34 that drives the scanner 32 on the basis of the scan drive signal generated in the signal generating unit 33.

The optical fiber 31 extends in the longitudinal direction inside the insertion portion 6, and the distal end of the optical fiber 31 is disposed at the distal end portion of the insertion portion 6.

Figure 6:
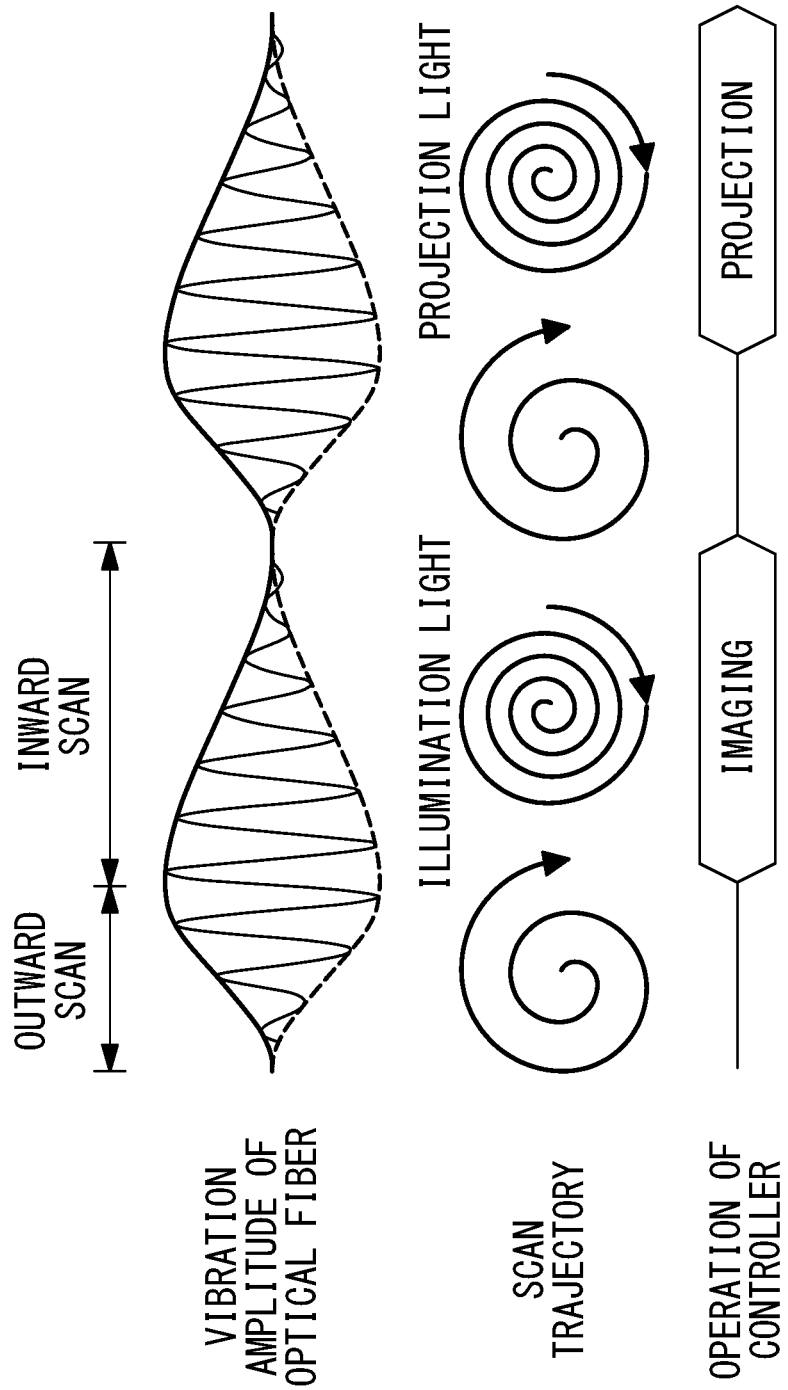
FIG. 6 is a diagram illustrating changes in the amplitude of the distal end of an optical fiber over time (top part), the scan trajectories of illumination light and projection light (middle part), and the operation timing chart (bottom part) for the optical scanning imaging/projection apparatus illustrated in FIG. 5.

The scanner 32 is, for example, an optical fiber scanner that scans the illumination light and the projection light by causing the distal end of the optical fiber 31 to vibrate in the radial direction of the optical fiber 31. As illustrated in FIG. 6, the scanner 32 is driven by the scanner driver 34 so that the distal end of the optical fiber 31 undergoes spiral vibration along a predetermined spiral trajectory within a substantially flat surface orthogonal to the longitudinal direction of the optical fiber 31. As a result, the illumination light and the projection light emitted from the distal end of the insertion portion 6 spirally scan the subject A along a predetermined spiral scanning trajectory T.

In FIG. 6, the top part shows the changes in amplitude of the spirally vibrating distal end of the optical fiber 31 over time in one direction. The middle part shows the scanning trajectory T of the illumination light and the projection light on the subject A. The bottom part shows the operation of the optical scanning imaging/projection apparatus 1. As shown in the top part and the middle part in FIG. 6, in spiral scanning, an outward scan in which light is scanned from the center of the scanning trajectory T toward the outer side and an inward scan in which light is scanned from the outer side of the scanning trajectory T toward the center are alternately repeated.

The scanner 32 is not limited to an optical fiber scanner and may be any other type of scanner (for example, a galvanometer mirror scanner). The scanning trajectory T is not limited to a spiral trajectory and may take any other shape (for example, a raster shape or a Lissajous shape).

The optical detection unit 40 is equipped with a light-receiving optical fiber 41 disposed inside the insertion portion 6; and an optical filter 42, an optical sensor 43, and an analog-digital converter (A/D converter) 44 disposed inside the controller device (controller) 7.

The distal end of the optical fiber 41 is disposed at the distal end surface of the insertion portion 6, and the proximal end of the optical fiber 41 is coupled to the controller device 7. The distal end surface of the optical fiber 41 receives the fluorescence (observation light) generated by the subject A irradiated with the illumination light, and the optical fiber 41 guides the received fluorescence into the controller device 7. In order to increase the amount of the fluorescence received, multiple optical fibers 41 are preferably disposed in the insertion portion 6.

The optical filter 42 is an excitation light cut filter having transmitting properties such that the fluorescence is selectively transmitted and light other than the fluorescence (illumination light and white light) is blocked. The optical filter 42 is disposed between the proximal end of the optical fiber 41 and the optical sensor 43, and, of the light received by the optical fiber 41, only the fluorescence enters the optical sensor 43.

The optical sensor 43 receives the fluorescence that has passed through the optical filter 42, converts the received fluorescence into electrical energy so as to generate an electrical signal with a magnitude corresponding to the intensity of the fluorescence, and outputs the generated electrical signal to the A/D converter 44.

The A/D converter 44 samples the electrical signal input from the optical sensor 43 at a predetermined sampling cycle, and converts the sampled electrical signal into a digital value so as to obtain a digital value (intensity value) indicating the intensity of the fluorescence. The A/D converter 44 sends the obtained intensity value to the storage unit 50.

The optical detection unit 40 is controlled by the main controller unit 70 so that the operation of detecting the observation light described above is executed only during the inward scan. As a result, imaging of the fluorescence is executed only during the inward scan, and the intensity value for one frame is obtained. In this embodiment, the period during which the scanning trajectory T is scanned inward and outward one time constitutes the one frame cycle.

Figures 7, 8:
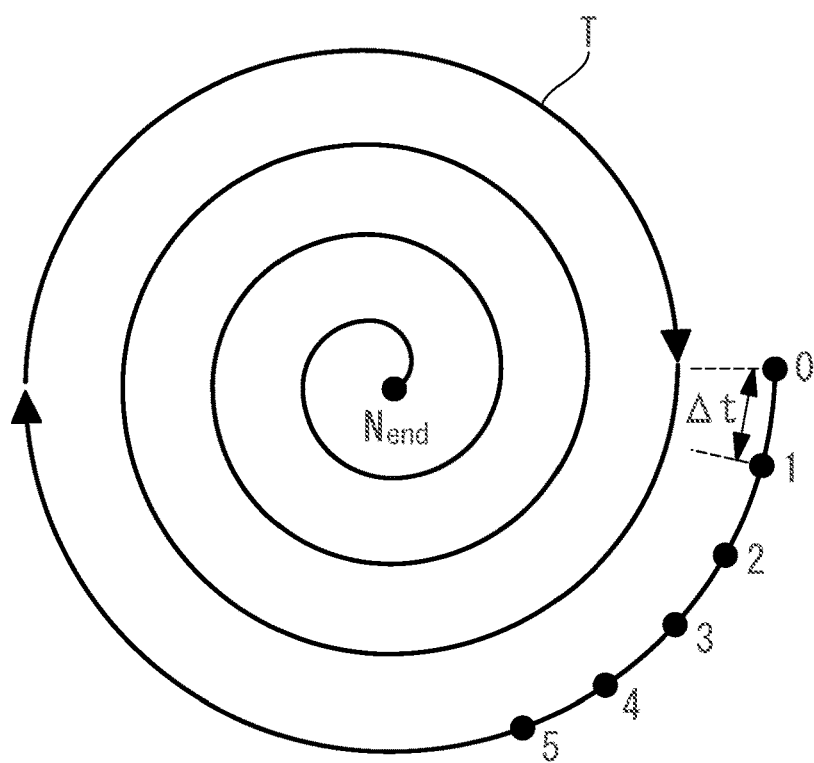
FIG. 7 illustrates one example of a data table stored in a storage unit.
FIG. 8 is a diagram illustrating the address in the data table illustrated in FIG. 7.

As illustrated in FIG. 7, the storage unit 50 stores, in association with the address N indicating the detection position of the observation light on the scanning trajectory T, the intensity value $D_N$ of the observation light received from the A/D converter 44 so as to generate data in a table form (data table). As illustrated in FIG. 8, the address involves the order in which the observation light is detected with the optical detection unit 40 during one inward scan period, i.e., order N=0, 1, 2, . . . , $N_{end}$. At corresponds to the sampling cycle. In the data table, the intensity values are arrayed in the order of detection. After the intensity value corresponding to the last address, $N_{end}$, is stored, the storage unit 50 resets the address to 0. In this manner, the data table is renewed every one frame cycle unit so that, in the data table, the intensity values from the last imaging are recorded.

The format of the data stored in the storage unit 50 may be any format as long as three items, i.e., the sampling order, the detection position information, and the intensity value, can be stored in association with one another. The format is not limited to the table form illustrated in FIG. 7 and may be in any other form.

The illumination light controlling unit 61 generates an illumination light control signal and sends the illumination light control signal to the switching unit 20.

The projection light controlling unit 62 generates a projection light control signal and sends the projection light control signal to the switching unit 20.

Here, from the data table in the storage unit 50, the projection light controlling unit 62 reads out the intensity values $D_N$ in ascending order of the address N associated with the intensity values. Then, the intensity of the projection light is calculated by using the read-out intensity value $D_N$ and the preset function $F(D_N)$. Then, a projection light control signal for outputting projection light that has the calculated intensity is generated. The function $F(D_N)$ is set such that the intensity of the projection light increases with the intensity value $D_N$. In other words, the projection light controlling unit 62 controls the projection laser light source 12 so that intense projection light is applied to the position at which intense fluorescence was detected, weak projection light is applied to the position at which weak fluorescence was detected, and the projection light is not applied to the position at which no fluorescence was detected. In this manner, the projection image of the fluorescence image obtained in the last imaging is formed on the subject A by using the projection light.

The main controller unit 70 controls the switching unit 20 such that the output to the laser driver 14 is switched between the illumination light control signal and the projection light control signal every one frame cycle unit. In other words, as illustrated in the bottom part in FIG. 6, the main controller unit 70 controls the light source unit 10 such that illumination light and the projection light are alternately scanned every one frame cycle unit. In this manner, the operation of imaging the fluorescence image on the subject A and the operation of projecting the imaged fluorescence image onto the subject A are executed alternately every one frame cycle unit.

Next, the effects of the endoscope system 100 having the above-described features are described.

In order to observe the inside of the body by using the endoscope system 100 of this embodiment, the endoscope body 4 is inserted into the body. Then, the insertion portion 6 of the optical scanning imaging/projection apparatus 1 is inserted into the body through the treatment tool channel 4a of the endoscope body 4. Then, the insertion portion 6 is disposed so that the imaging range of the optical scanning imaging/projection apparatus 1 (scan range of the illumination light) lies within the imaging range of the endoscope apparatus 2, and the operation of the optical scanning imaging/projection apparatus 1 is started.

Figure 9:
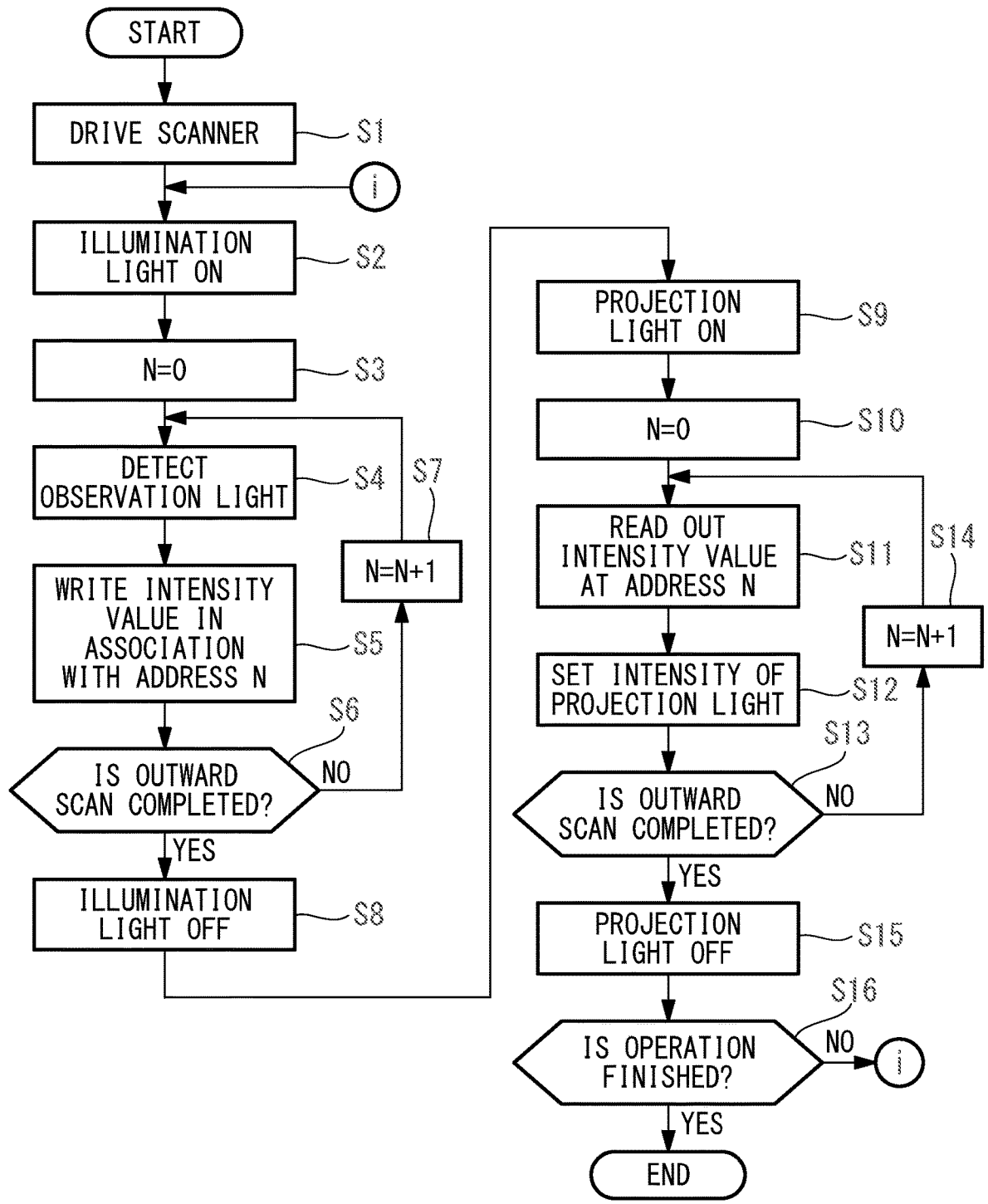
FIG. 9 is a flowchart illustrating the operations of the optical scanning imaging/projection apparatus illustrated in FIG. 5.

As illustrated in FIG. 9, the main controller unit 70 starts driving of the optical scanning unit 30 (step S1), and then executes the operation of imaging the fluorescence image (steps S2 to S8) and the operation of projecting the fluorescence image (steps S9 to S15) alternately for every one frame cycle unit.

In the imaging operation, the main controller unit 70 controls the switching unit 20 so that illumination light is output from the light source unit 10 (step S2). In this manner, the illumination light is scanned on the subject A, the fluorescence generated at the position irradiated with the illumination light is detected with the optical detection unit 40 (step S4), and the intensity value of the detected fluorescence, in association with the detection order N (steps S3 and S7), is stored in the data table in the storage unit 50 (step S5).

Once the outward scan is completed (YES in step S6), the main controller unit 70 controls the switching unit 20 so that the output from the light source unit 10 is switched from the illumination light to the projection light (steps S8 and S9). As a result, the imaging operation ends, and the projection operation starts.

In the projection operation, the projection light controlling unit 62 reads out the intensity values of the fluorescence from the data table in the storage unit 50 in the ascending order of the address (steps S10, S11, and S14). Then, the intensity of the projection light is set on the basis of the read-out intensity values (step S12), and controls the intensity of the projection light to the set intensity. In this manner, the fluorescence image on the subject A imaged in the last scan is projected by the projection light. The projected image is imaged by using the endoscope body 4, and the endoscope body 4 acquires an endoscopic image in which the white-light image and the projected image of the subject A are superimposed on each other.

Once the outward scan is completed (YES in step S13), the switching unit 20 controls the switching unit 20 so that the output from the light source unit 10 is switched from the projection light to the illumination light (steps S15 and S2). As a result, the projection operation ends, and the next imaging operation starts.

Since the projection light is visible light, the user can observe the projected image in the endoscopic image displayed on the display apparatus 3. Thus, by using a fluorescent dye that accumulates in a region within the body tissue (for example, a lesion or a blood vessel) that is difficult to observe in a white-light image, this region can be observed as a projected image in the endoscopic image.

In this case, according to this embodiment, because the same optical system is used to image and project the fluorescence image, the projection light is applied to the same position where the fluorescence is detected. In particular, since both imaging and projection are performed during the inward scan, the illumination light and the projection light are scanned along the same scanning trajectory T, and thus the fluorescence detection position and the projection light application position accurately coincide with each other. Thus, the projected image having the same shape as the imaged fluorescence image is formed at the same position as the imaged fluorescence image, and the positional relationship between the white-light image and the projected image of the subject A is always accurate within the endoscopic image. As such, an advantage is afforded in that an endoscopic image in which a fluorescence image having a color of the projection light is superimposed on a white-light image without positional displacement can be obtained without using a special sophisticated processor.

By switching between imaging and projection every one frame cycle unit at a high speed, the imaged fluorescence image can be projected on a real-time basis, and even when the subject A is moving, the projected image can be accurately positioned relative to the subject A.

In this embodiment, the main controller unit 70 executes the imaging operation and the projection operation during the inward scan; however, the timing of performing the imaging operation and the projection operation is not limited to this.

For example, the imaging operation and the projection operation may be executed during the outward scan.

Figure 10:
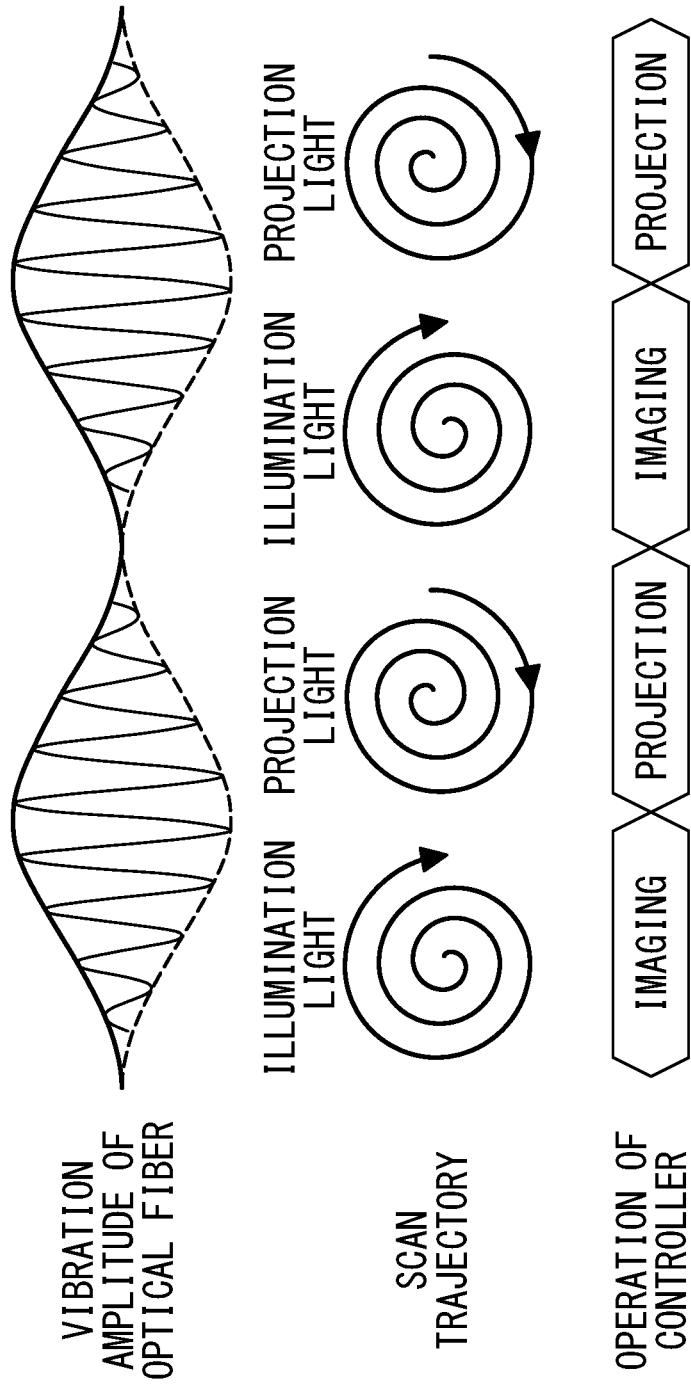
FIG. 10 is a diagram illustrating a modified example of changes in the amplitude of the distal end of an optical fiber over time (top part), the scan trajectories of illumination light and projection light (middle part), and the operation timing chart (bottom part) for the optical scanning imaging/projection apparatus illustrated in FIG. 5.

Alternatively, as illustrated in FIG. 10, the imaging operation may be executed during the outward scan and the projection operation may be executed during the inward scan. In such a case, the optical scanning unit 30 is controlled so that the scanning trajectory of the illumination light during the outward scan substantially coincides with the scanning trajectory of the projection light during the inward scan.

Instead of switching between the imaging operation and the projection operation every one frame cycle, at least one of the imaging operation and the projection operation may be continuously executed for more than one frame cycle.

Figure 11A:
FIG. 11A is a timing chart illustrating another modified example of the operations of the optical scanning imaging/projection apparatus illustrated in FIG. 5.
Figure 11B:
FIG. 11B is a timing chart illustrating yet another modified example of the operations of the optical scanning imaging/projection apparatus illustrated in FIG. 5.

For example, as illustrated in FIG. 11A, multiple frame cycles of the imaging operation and one frame cycle of the projection operation may be alternately executed. When the imaging operation is continuously executed in this way, the amount of fluorescence received from each detection position can be increased, and weak fluorescence can be detected with high sensitivity. Alternatively, as illustrated in FIG. 11B, one frame cycle of the imaging operation and multiple frame cycles of the projection operation may be alternately executed. In this manner, the amount of light during projection can be increased, and the visibility of the projected image can be improved.

In this embodiment, the projection light intensity settings in the projection light controlling unit 62 may be changed according to the number of times projection is performed.

In this embodiment, excitation light is output as the illumination light from the illuminating laser light source 11; alternatively, infrared light, narrow-band light, or white light may be output as the illumination light.

When the illumination light is infrared light, the reflected infrared light is detected as the observation light. Thus, in such a case, an optical filter 42 that has properties that selectively transmit infrared light is used. By using the infrared light as the illumination light, a blood vessel image in the body tissue can be acquired, and the blood vessel image can be projected.

When the illumination light is narrow-band light, the reflected narrow-band light is detected as the observation light. Thus, in such a case, an optical filter 42 that has properties that selectively transmit narrow-band light is used. When multiple beams of narrow-band light are used as the illumination light, the color of the projection light is preferably complementary to the color constituted by the multiple beams of the narrow-band light. For example, when blue and red beams of narrow-band light are used, purple light is applied to the subject A. In such a case, green projection light is preferably used. During projection, an afterimage of the illumination light applied to the subject A during the last imaging appears in the eyes of the user. By using projection light of a color complementary to the color of the illumination light, the visibility of the projected image can be improved.

Figure 12:
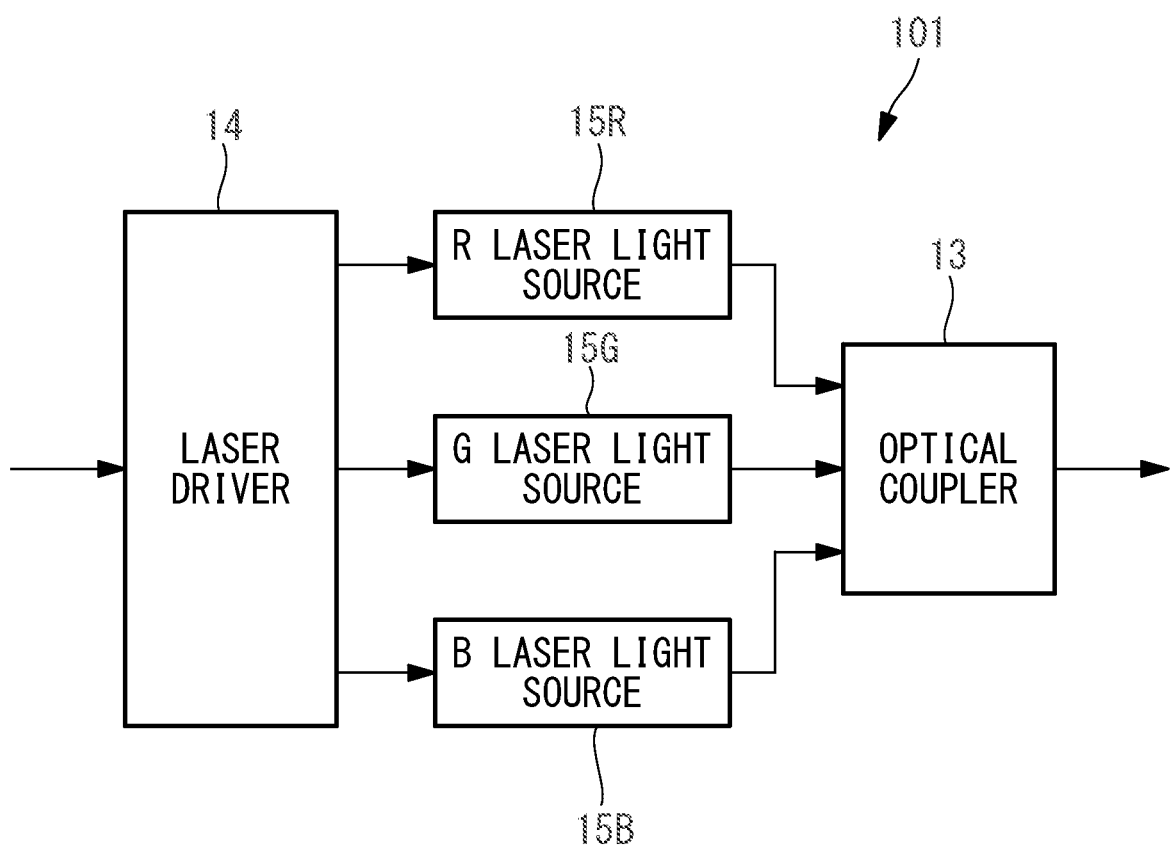
FIG. 12 is a diagram illustrating a modified example of the light source unit in the optical scanning imaging/projection apparatus illustrated in FIG. 5.

Alternatively, as illustrated in FIG. 12, a light source unit 101 may be equipped with three laser light sources 15R, 15G, and 15B that respectively output red (R), green (G), and blue (B) laser beams, at least one of which may be used as the illuminating laser light source and at least one of which may be used as the projection laser light source.

An example of the application of the light source unit 101 is projection of an image of a blood vessel.

Hemoglobin strongly reflects red light and strongly absorbs blue light, and thus, the difference between the intensity of the red reflected light and the intensity of the blue reflected light differs between the position where a blood vessel is present and the position where a blood vessel is not present. Thus, in the imaging operation, red illumination light and blue illumination light are applied to the subject A so as to detect red reflected light and blue reflected light, and the difference between the intensity of red reflected light and blue reflected light is calculated so as to identify, on the basis of the difference, the position where a blood vessel is present. In the projection operation, by applying green projection light to the identified position, a clear image of the blood vessel can be projected onto the subject A.

Figure 13:
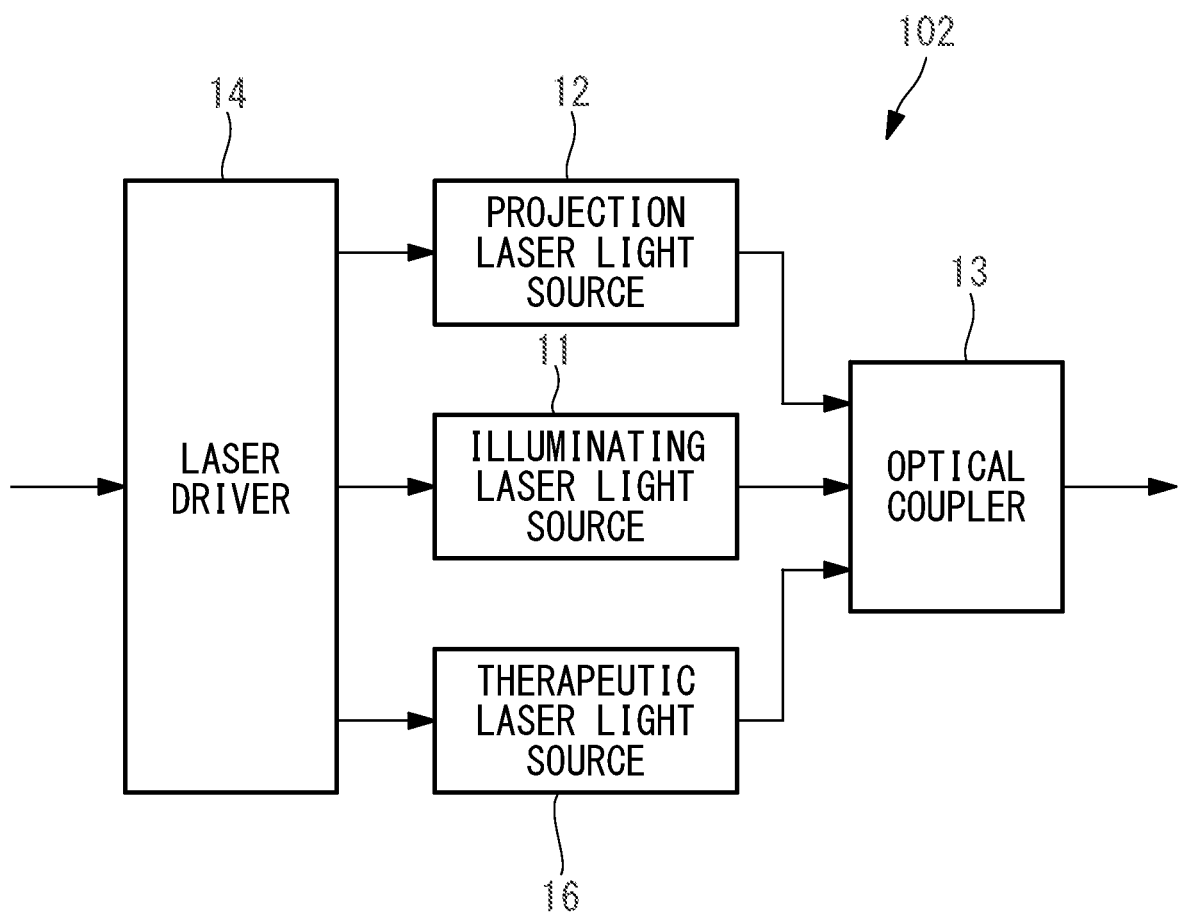
FIG. 13 is a diagram illustrating another modified example of the light source unit in the optical scanning imaging/projection apparatus illustrated in FIG. 5.

In this embodiment, as illustrated in FIG. 13, a light source unit 102 may be further equipped with a therapeutic laser light source 16 that outputs therapeutic light. The therapeutic light is a laser beam for treating body tissue.

Figure 14A:
FIG. 14A is a timing chart illustrating an example of the operations of the optical scanning imaging/projection apparatus equipped with the light source unit illustrated in FIG. 13.
Figure 14B:
FIG. 14B is a timing chart illustrating another example of the operations of the optical scanning imaging/projection apparatus equipped with the light source unit illustrated in FIG. 13.

In such a case, a treatment that uses the therapeutic light may be performed in combination with the imaging of the observation light image and projection of the observation light image. In such a case, illumination light that enables observation of the site to be treated is preferably used. For example, excitation light is applied to the site to be treated where a fluorescent substance is accumulated. Then, as illustrated in FIGS. 14A and 14B, treatment, imaging, and projection are performed one after another; as a result, the effect of the treatment can be checked on a real-time basis by using the projected fluorescence image, and the therapeutic light can be controlled on the basis of the effect of the treatment. When the treatment and imaging are performed one after another, the color of the therapeutic light and the color of the illumination light are preferably complementary to each other.

Figure 14C:
FIG. 14C is a timing chart illustrating another example of the operations of the optical scanning imaging/projection apparatus equipped with the light source unit illustrated in FIG. 13.

When the same laser beam is used as the therapeutic light and the illumination light, as illustrated in FIG. 14C, treatment and imaging may be performed simultaneously.

Figure 16:
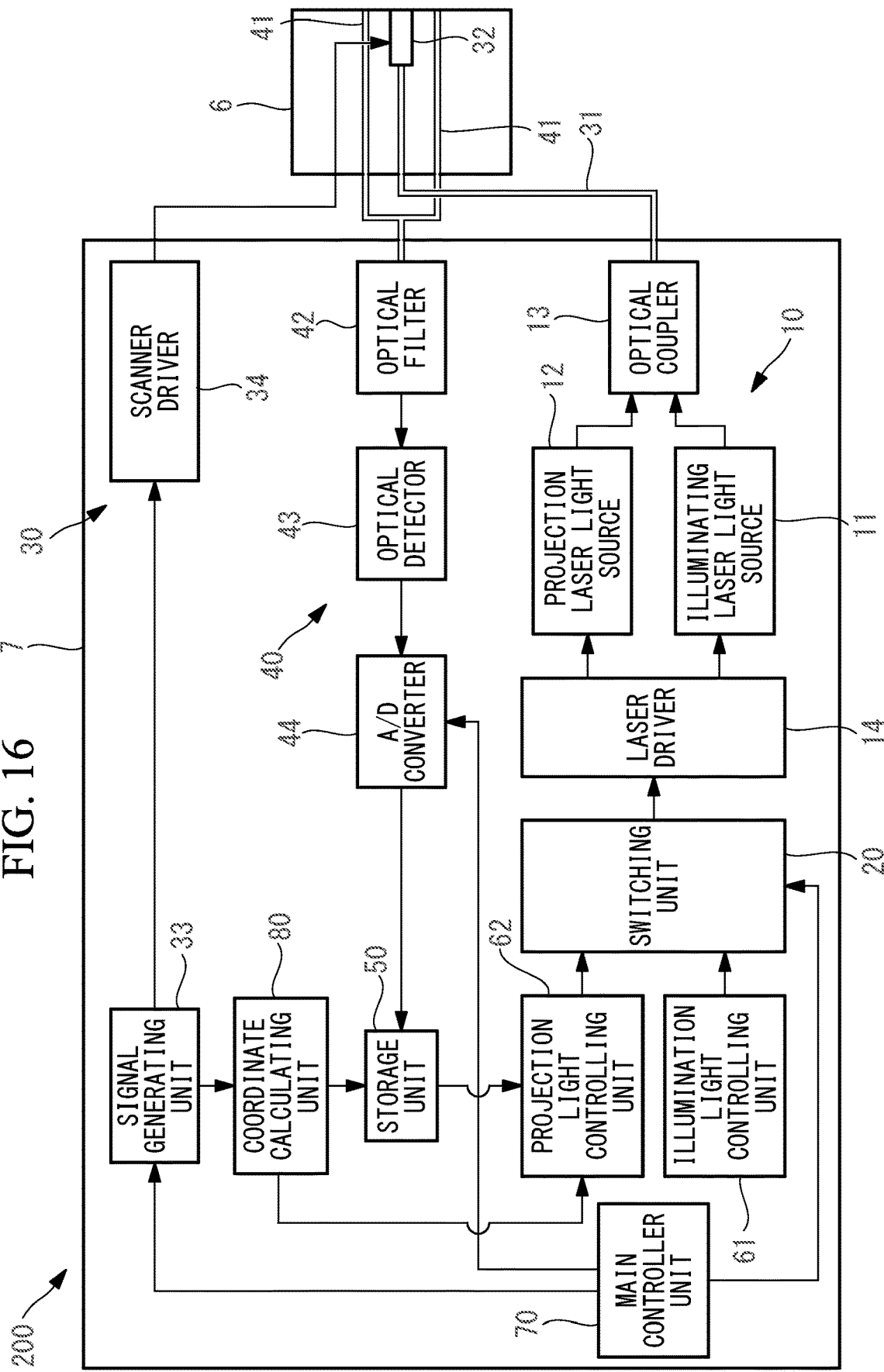
FIG. 16 is diagram showing the overall configuration of a modified example of the optical scanning imaging/projection apparatus illustrated in FIG. 5.

In this embodiment, in the data table, the intensity value of the observation light is associated with the order N in which the observation light is detected; alternatively, as illustrated in FIG. 15, the intensity value may be associated with the two-dimensional coordinates of the position where the observation light is detected. In such a case, as illustrated in FIG. 16, an optical scanning imaging/projection apparatus 200 is further equipped with a coordinate calculating unit (coordinate calculator) 80 that calculates the two-dimensional coordinates of each detection position.

Figure 17:
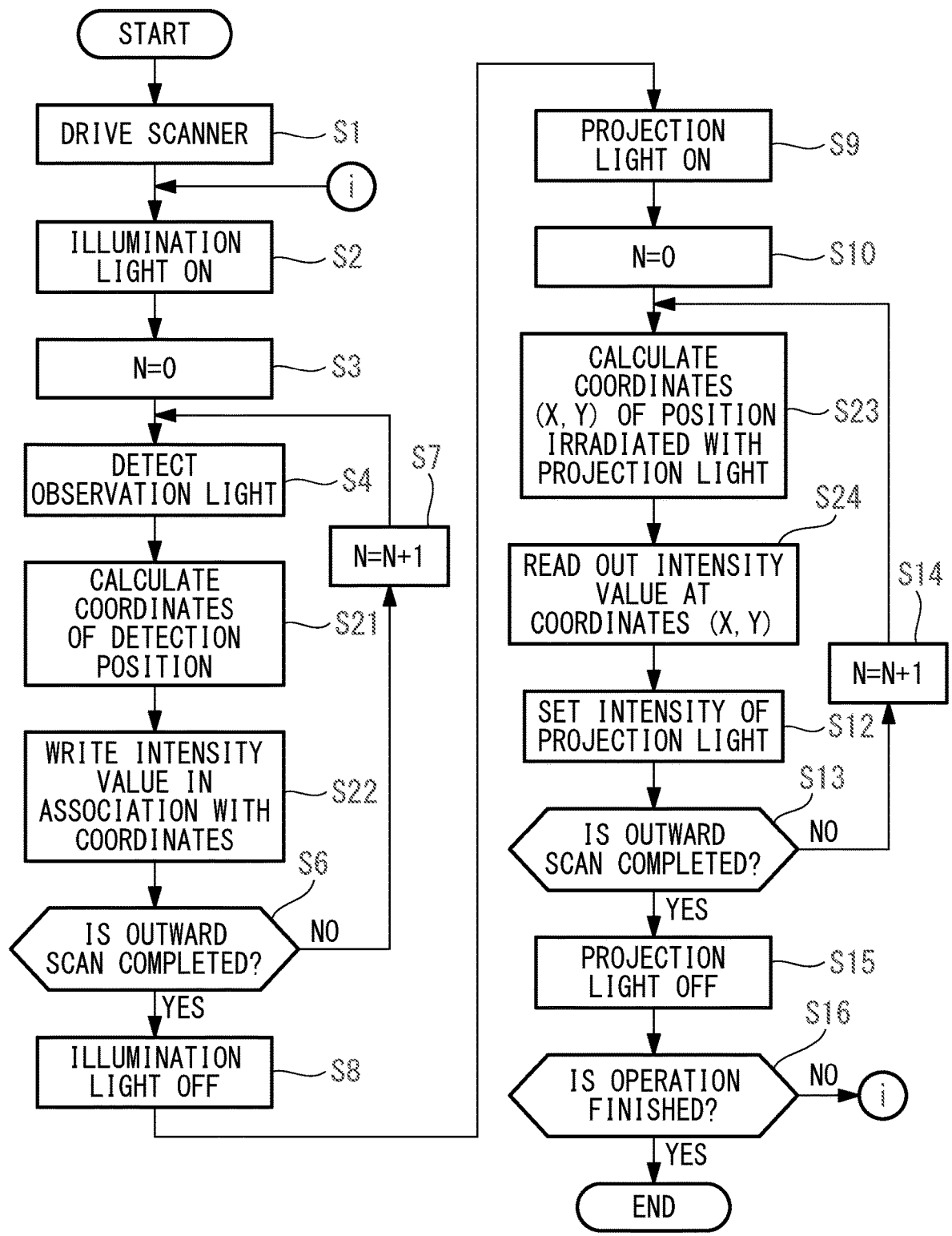
FIG. 17 is a flowchart illustrating the operations of the optical scanning imaging/projection apparatus illustrated in FIG. 16.

FIG. 17 illustrates the operations in this modification. During the imaging operation, the coordinate calculating unit 80 receives a scan drive signal from the signal generating unit 33, computes, from the drive signal, the coordinates of the detection position, which is the position of the illumination light on the scanning trajectory T at each detection time (step S21), and sends the calculated coordinates to the storage unit 50. In the data table, the coordinates of detection position of the observation light and the intensity are recorded in association with each other (step S22). Thus, two-dimensional image data of the observation light is generated as a data table.

During the projection operation, the coordinate calculating unit 80 receives a scan drive signal from the signal generating unit 33, calculates the coordinates (X, Y) of the position of the projection light on the scanning trajectory T (step S23), and sends the calculated coordinates to the projection light controlling unit 62. The projection light controlling unit 62 reads out the intensity value $D_{(X, Y)}$ associated with the coordinates (X, Y) from the storage unit 50 (step S24), and calculates the intensity of the projection light from the function $F(D_{(X, Y)})$ by using the intensity value $D_{(X, Y)}$.

Figure 18:
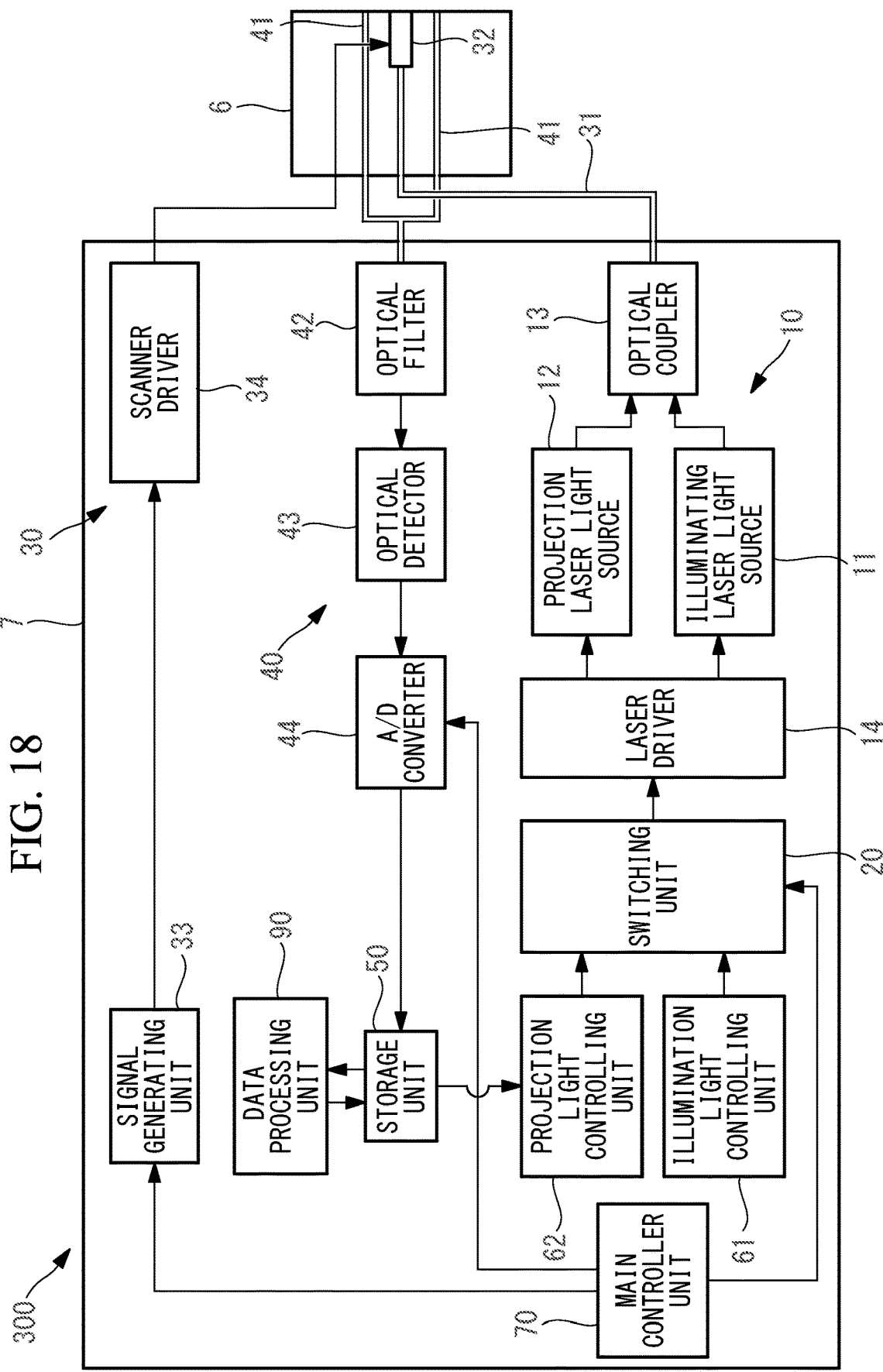
FIG. 18 is diagram showing the overall configuration of another modified example of the optical scanning imaging/projection apparatus illustrated in FIG. 5.

In this embodiment, as illustrated in FIG. 18, an optical scanning imaging/projection apparatus 300 may be further equipped with a data processing unit (data processor) 90 that processes the data table generated in the storage unit 50.

The data processing unit 90 processes the data table between the imaging operation and the projection operation (between step S8 and step S9). Thus, the projection light controlling unit 62 controls the intensity of the projection light on the basis of the data table processed by the data processing unit 90.

Data processing involves, for example, binarization of the intensity value or contrast enhancement. Through this process, the difference between the high intensity value and the low intensity value can be widened, and thus, the visibility of the projected image on the subject A can be improved.

When the data table is two-dimensional image data, the data processing unit 90 may perform various types of image processing, such as edge enhancement or denoising, on the data table in addition to binarization and contrast enhancement.

In this embodiment, the imaging operation and the projection operation are switched every frame cycle unit; alternatively, the imaging operation and the projection operation may be switched every time unit shorter than one frame cycle.

For example, when the imaging operation and the projection operation is switched every one detection cycle (sampling cycle) unit of the observation light by the optical detection unit 40 so that the illumination light and the projection light are alternately applied to the subject A during the same frame cycle, the real time properties of the projected image formed on the subject A can be further improved.

Alternatively, the imaging operation and the projection operation may be switched every scan cycle unit of the illumination light and the projection light by the optical scanning unit 30. The scan cycle is the orbit cycle (=1/vibration frequency of optical fiber 31) in spiral scanning.

In the embodiments described above, the projection light controller 62 can be realized by hardware such as one or more Central Processing Unit (CPU), and by reading instructions stored on a computer readable storage device.

As a result, the following aspect is read from the above described embodiment of the present invention.

A first aspect of the present invention provides an optical scanning imaging/projection apparatus that includes a light source that is configured to output illumination light and projection light, the projection light being in the visible range; an optical scanner that is configured to scan the illumination light and the projection light, which are output from the light source, along a predetermined scanning trajectory; a switch that is configured to switch the output from the light source so that the illumination light and the projection light are alternately output; an optical detector that is configured to detect observation light generated by a subject irradiated with the illumination light; a storage that is configured to store data in which an intensity of the observation light detected with the optical detector is associated with information indicating a detection position on the scanning trajectory; and a projection light controller that is configured to control an intensity of the projection light to be applied to each position on the scanning trajectory, wherein the projection light controller comprises one or more processors, the one or more processors are configured to control the intensity of the projection light on the basis of the data stored in the storage.

According to the present invention, the illumination light output from the light source is scanned on the subject by the optical scanner, the observation light generated by the subject is detected with the optical detector, and the intensity of the detected observation light associated with the information indicating the detection position is stored in the data in the storage. Thus, the observation light image generated by the subject is imaged, and the data indicating the intensity distribution of the observation light image on the subject is acquired.

Next, the switch switches the output from the light source to the projection light, and the projection light is scanned on the subject by the optical scanner. During this process, the intensity of the projection light applied to each position on the scanning trajectory is controlled by the projection light controller on the basis of the intensity of the observation light in the data stored in the storage, and, thus, the observation light image is projected onto the subject by using the projection light.

Since the positions irradiated with the illumination light and the projection light scanned by the same optical scanner accurately coincide with each other, the projection light having an intensity corresponding to the intensity of the observation light can be accurately applied to the position on the subject where the observation light has been generated. In this manner, the projected image, which is formed by the projection light in the visible range and which has the same shape as the observation light image, is formed on the subject and at the same position as the position where the observation light image is formed. By observing the thus-formed projected image on the subject by using an observation device that uses light different from the illumination light, two types of subject images superimposed on each other without displacement can be observed without using a special sophisticated processor.

In the first aspect described above, the switch may switch between the illumination light and the projection light every frame cycle unit.

The frame cycle refers to the cycle in which the illumination light scans the predetermined scanning trajectory once. In this manner, imaging and projection of the observation light image can be switched at a high speed, and the real-time properties of the projected image can be improved.

In the first aspect described above, the switch may switch between the illumination light and the projection light either every detection cycle unit of the observation light by the optical detector or every scan cycle unit of the illumination light and the projection light by the optical scanner.

In this manner, imaging and projection of the observation light image can be switched within a time interval shorter than the frame cycle, and the real-time property of the projected image can be further improved.

In the first aspect described above, the light source may output, as the illumination light, excitation light that excites fluorescence contained in the subject, and the optical detector may be equipped with an excitation light cut filter that blocks the excitation light and transmits the fluorescence, and may detect the fluorescence that has passed through the excitation light cut filter.

In this manner, the fluorescence image can be imaged, and the fluorescence image can be projected by using the projection light in the visible range.

In the first aspect described above, the light source may output, as the illumination light, infrared light.

In this manner, the infrared image can be imaged, and the infrared image can be projected by using the projection light in the visible range.

In the first aspect described above, the light source may output therapeutic light for treating body tissue, and the switch may switch the output of the light source between the illumination light, the projection light, and the therapeutic light.

In this manner, a treatment by using the therapeutic light can be performed at the same time as the observation of the observation light image.

In the first aspect described above, the storage may store the order in which the observation light is detected with the optical detector as the information indicating the detection position, and may array the intensity of the observation light in accordance with the order within the data, and the projection light controller may control the intensity of the projection light according to the order of the intensity of the observation light within the data.

In this manner, the process of generating data and controlling the intensity of the projection light can be simplified.

In the first aspect described above, the optical scanning imaging/projection apparatus may further include a coordinate calculator that calculates coordinates of the detection position of the observation light detected with the optical detector, and the storage may store the coordinates calculated by the coordinate calculator as the information indicating the detection position.

In this manner, two-dimensional image data can be generated as the data in the storage.

In the first aspect described above, the optical scanning imaging/projection apparatus according may further include a data processor that processes the data stored in the storage, and the projection light controller may control the intensity of the projection light on the basis of the data processed by the data processor.

In this manner, the intensity-related data in the data can be processed so that the visibility of the projected image on the subject is improved.

A second aspect of the present invention provides an endoscope system that includes any of the optical scanning imaging projection apparatuses described above, and an endoscope apparatus that acquires an endoscopic image of the subject.

REFERENCE SIGNS LIST 1, 200, 300 optical scanning imaging/projection apparatus
2 endoscope apparatus
3 display apparatus
4 endoscope body
4a treatment tool channel
5 processor
6 insertion portion
7 controller device (controller)
10, 101, 102 light source unit (light source)
11 illuminating laser light source
12 projection laser light source
13 optical coupler
14 laser driver
15R, 15G, 15B laser light source
16 therapeutic laser light source
20 switching unit (switch)
30 optical scanning unit (optical scanner)
31 optical fiber
32 scanner
33 signal generating unit (signal generator)
34 scanner driver
40 optical detector
41 optical fiber
42 optical filter
43 optical sensor
44 A/D converter
50 storage
61 illumination light controlling unit (illumination light controller)
62 projection light controlling unit (projection light controller)
70 main controller unit (main controller)
80 coordinate calculating unit (coordinate calculator)
90 data processing unit (data processor)
100 endoscope system
S scanning trajectory

The invention claimed is:

1. An optical scanning imaging/projection apparatus comprising:

a light source configured to output illumination light and projection light, said projection light being in the visible range;

an optical scanner provided at a distal end portion of an elongated insertion portion to be inserted into a body, the optical scanner being configured to radiate, on body tissue, the illumination light and the projection light output from the light source by using an optical fiber scanner that vibrates a tip of an optical fiber along scanning trajectories with light scanning in an outward spiral and in an inward spiral;

a switch configured to switch the output from the light source so that the illumination light and the projection light are alternately output;

an optical detector configured to detect observation light generated by a subject irradiated with the illumination light;

a storage configured to store data in which an intensity of the observation light detected with the optical detector is associated with information indicating a detection position on the scanning trajectories; and a projection light controller configured to control an intensity of the projection light to be applied to each position on the scanning trajectories, wherein the projection light controller comprises one or more processors, the one or more processors are configured to control the intensity of the projection light on the basis of the data stored in the storage, and the switch is configured to switch between the illumination light in the outward spiral and the projection light in the inward spiral.

2. The optical scanning imaging/projection apparatus according to claim 1, wherein the switch switches between the illumination light and the projection light either every detection cycle unit of the observation light by the optical detector or every scan cycle unit of the illumination light and the projection light by the optical scanner.

3. The optical scanning imaging/projection apparatus according to claim 1, wherein the light source outputs, as the illumination light, excitation light that excites fluorescence contained in the subject, and the optical detector is equipped with an excitation light cut filter that blocks the excitation light and transmits the fluorescence, and detects the fluorescence that has passed through the excitation light cut filter.

4. The optical scanning imaging/projection apparatus according to claim 1, wherein the light source outputs infrared light as the illumination light.

5. The optical scanning imaging/projection apparatus according to claim 1, wherein the light source outputs therapeutic light for treating body tissue, and the switch switches the output of the light source between the illumination light, the projection light, and the therapeutic light.

6. The optical scanning imaging/projection apparatus according to claim 1, wherein the storage stores the order in which the observation light is detected with the optical detector as the information indicating the detection position, and arrays the intensity of the observation light in accordance with the order within the data, and the one or more processors control the intensity of the projection light according to the order of the intensity of the observation light within the data.

7. The optical scanning imaging/projection apparatus according to claim 1, further comprising a coordinate calculator configured to calculate coordinates of the detection position of the observation light detected with the optical detector, wherein the storage stores the coordinates calculated by the coordinate calculator as the information indicating the detection position.

8. The optical scanning imaging/projection apparatus according to claim 1, further comprising a data processor configured to process the data stored in the storage, wherein the one or more processors controls the intensity of the projection light on the basis of the data processed by the data processor.

9. An endoscope system comprises:

the optical scanning imaging/projection apparatus according to claim 1, and an endoscope apparatus configured to acquire an endoscopic image of the subject illuminated by one or more of the illumination light and the projection light.

10. The endoscope system according to claim 9, wherein:

an imaging range of the optical scanning imaging/projection apparatus lies within an imaging range of the endoscope apparatus, and the endoscope apparatus is configured to acquire the endoscopic image including a projected image by the projection light output from the optical scanning imaging/projection apparatus.

11. The endoscope system according to claim 9, further comprising a display configured to display the endoscopic image acquired by the endoscope apparatus, the display being configured to display the endoscopic image including a projected image by the projection light output from the optical scanning imaging/projection.

12. The optical scanning imaging/projection apparatus according to claim 1, wherein, in the optical scanner, a scanning trajectory of the illumination light in the outward spiral and a scanning trajectory of the projection light in the inward spiral have a substantially same shape.

13. A method for an optical scanning imaging/projection, the method comprising:

inserting an elongated insertion portion into a body;

radiating, on body tissue, illumination light and projection light by using an optical fiber scanner provided at a distal end of the insertion portion along trajectories for light-scanning in an outward spiral and in an inward spiral different from the first direction;

detecting observation light generated by a subject irradiated with the illumination light; and controlling an intensity of the projection light to be applied to each position on the scanning trajectories based on data in which an intensity of the detected observation light is associated with information indicating a detection position on the scanning trajectories, wherein the illumination light and the projection light are alternately radiated such that the illumination light is radiated in the outward spiral, and the projection light is radiated in the inward spiral.

14. The method according to claim 13, further comprising acquiring an endoscopic image including a projected image by the projection light.

15. The method according to claim 13, wherein a scanning trajectory of the illumination light in the outward spiral and a scanning trajectory of the projection light in the inward spiral have a substantially same shape.

* * * * *